United States Patent
Teppke

(10) Patent No.: US 8,007,719 B2
(45) Date of Patent: Aug. 30, 2011

(54) METHOD AND DEVICE FOR DISINFECTING A MICROTOME CRYOSTAT

(75) Inventor: Dieter Teppke, Schwetzingen (DE)

(73) Assignee: Microm International GmbH, Walldorf (DE)

( * ) Notice: Subject to any disclaimer, the term of this patent is extended or adjusted under 35 U.S.C. 154(b) by 0 days.

(21) Appl. No.: 12/656,659

(22) Filed: Feb. 12, 2010

(65) Prior Publication Data

US 2010/0329925 A1 Dec. 30, 2010

(30) Foreign Application Priority Data

Jun. 25, 2009 (DE) .......................... 10 2009 030 624

(51) Int. Cl.
*A61L 2/00* (2006.01)
*A61L 9/00* (2006.01)

(52) U.S. Cl. ........................................... 422/28; 422/30

(58) Field of Classification Search .................... 422/28, 422/30
See application file for complete search history.

(56) References Cited

U.S. PATENT DOCUMENTS

| | | | |
|---|---|---|---|
| 3,233,965 A | 2/1966 | McCormick | |
| 6,481,219 B2 * | 11/2002 | Palermo | 62/51.1 |
| 7,287,388 B2 * | 10/2007 | Dorenkamp et al. | 62/51.1 |
| 2002/0139124 A1 * | 10/2002 | Palermo | 62/51.1 |
| 2005/0098563 A1 | 5/2005 | Kunkel | |
| 2006/0123800 A1 * | 6/2006 | Metzner | 62/51.1 |
| 2006/0133950 A1 * | 6/2006 | Teppke | 422/28 |
| 2008/0181814 A1 | 7/2008 | Teppke | |
| 2010/0233020 A1 * | 9/2010 | Klaassen et al. | 422/20 |

FOREIGN PATENT DOCUMENTS

| | | |
|---|---|---|
| DE | 689 08 857 | 1/1994 |
| DE | 103 24 646 | 12/2004 |
| FR | 2 705 587 | 12/1994 |

OTHER PUBLICATIONS

Anglia Scientific Company Broshure, "As 600 Cryotome", Cambridge, England (2009).

* cited by examiner

*Primary Examiner* — Robert J Warden
(74) *Attorney, Agent, or Firm* — Paul Vincent

(57) ABSTRACT

A device and a method for disinfecting a microtome cryostat with introduction of a disinfection agent (3) into the cryostat chamber (2), action of the disinfection agent on the cryostat chamber, removal of the disinfection agent (3) by precipitation in a colder area (6) and drainage away from there. To enable such a microtome cryostat (1) to be disinfected several times per day without prolonged interruption of operation, a disinfection agent is used (3) that is effective below 0° C. and is introduced as a mist into the cryostat chamber (2) at below 0° C., the disinfection agent (3) being effective as a frost deposit in the cryostat chamber, wherein the frost deposit is displaced into a colder area (6) by sublimation and is converted to liquid by sporadic defrosting phases of this area (6) and thus removed.

29 Claims, 1 Drawing Sheet

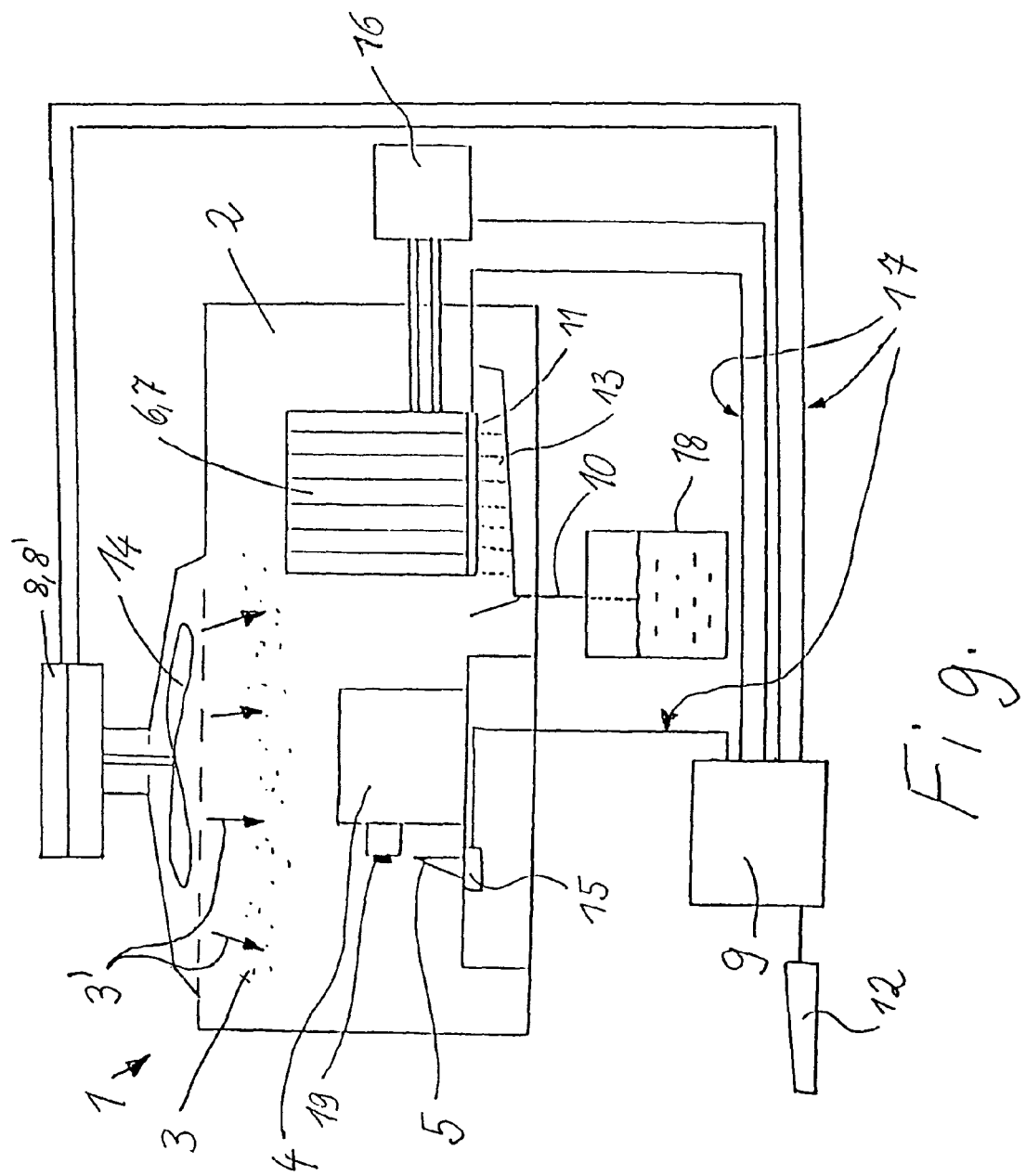

METHOD AND DEVICE FOR DISINFECTING A MICROTOME CRYOSTAT

This application claims Paris Convention priority of DE 10 2009 030 624.2 filed Jun. 25, 2009 the complete disclosure of which is hereby incorporated by reference.

BACKGROUND OF THE INVENTION

The invention relates to a method for disinfecting a microtome cryostat with
 a) Introduction of a disinfection agent into the cryostat chamber
 b) Action of the disinfection agent on the cryostat chamber
 c) Removal of the disinfection agent by precipitation in a colder area and drainage away from there.

The invention also relates to a device for disinfecting a microtome croyostat by a method of that type with a microtome, a cold generator, a facility for the provision and introduction of a disinfection agent into the cryostat chamber and a control.

Because microtomes are often used to section tissue specimens that are infected with germs, disinfection is a requirement for the protection of the operating personnel. The following proposals have been made for such disinfections:

One proposal for solving the problem in US 2002/0139124 A1 is to perform the disinfection with ozone. However, this has the disadvantage that ozone is very corrosive and damages surfaces by oxidation. A further disadvantage is that ozone residue is difficult to remove, is toxic, and is highly flammable, or can partially escape from the device during the disinfection phase, thus posing a hazard to operating personnel.

The brochure "AS 600 Cryotome" of the company ANGLIA SCIENTIFIC proposes another solution for decontamination using ultraviolet radiation. However, this has the disadvantage that the ultraviolet radiation does not penetrate into shaded regions. Moreover, there is no depth of penetration of the ultraviolet rays into section waste or specimen remnants, or into microscopically small depressions in metal surfaces. This method of decontamination is therefore unsatisfactory.

A method and a device of the type described in the introduction is proposed by DE 103 03 989 B4, wherein a vaporous disinfection agent is conveyed into a cryostat chamber that has previously been heated. After a disinfecting time, the disinfection agent is removed by the generation of a difference in temperature between the cryostat chamber and a cold generator, which causes the microtome, which preferably continues to be heated, to be dried and the entire disinfection agent is precipitated onto the cold generator which has been restarted. It is thawed and removed from there by reheating the cold generator. The cold generator is then restarted so that the cryostat chamber regains its operating temperature. This procedure was already considerably faster than drying out simply by leaving the cryostat open after disinfection until the cryostat chamber with microtome is dry. Nevertheless, it still takes at least two hours for the microtome to restart, this time period consisting of the defrosting and heating time, the provision and disinfecting time of the disinfection agent, and the time required to remove the disinfection agent, and for recooling. Therefore, disinfection can either only be performed at the end of a working day or, if a high risk of infection necessitates more frequent disinfection, a considerable restriction in the deployment of the microtome cryostat will result.

The object of this invention is therefore to provide a method and a device of the type stated in the introduction such that the microtome cryostat can be disinfected several times per day without prolonged interruption of operation.

SUMMARY OF THE INVENTION

The task is inventively solved by the following embodiment of the method steps described in the introduction.
 a) A disinfection agent that is effective below 0° C. is introduced as a mist into the cryostat chamber at below 0° C.,
 b) The disinfection agent is effective as a frost deposit in the cryostat chamber,
 c) The frost deposit is displaced into a colder area by sublimation and is then condensed by the sporadic defrosting phases of this area and thus drained away.

The object is solved by a device of the type described above, characterized in that the device for the provision and introduction of a disinfection agent is a nebulization device constituted such that a frost deposit of the disinfection agent can be obtained in the cryostat chamber due to its fineness and to the way in which the nebulized disinfection agent is introduced into the cryostat chamber at a temperature below 0° C., and characterized in that the control is constituted such that it causes the thawing of the disinfection agent that has precipitated and collected on the cold generator by sublimation before this layer has become so thick that it might impair the operation of the cold generator, and that a draining facility guides the thawed disinfection agent out of the cryostat chamber.

The invention is also based on the knowledge that several of the known disinfection agents also have disinfecting properties when they form a frost deposit by being introduced in nebulized form into a cryostat chamber at below 0° C. The invention makes use of this fact to effect disinfection.

The invention also makes use of the fact that such a frost deposit is removed again by sublimation even at a temperature below 0° C. if an even colder area exists. Precipitation of the disinfection agent in the even colder area ensures that the saturation sublimation pressure in the cryostat chamber is not reached and therefore the sublimation of the frost deposited disinfection agent continues until the entire disinfection agent has been precipitated in the colder area. This colder area is advantageously the microtome cryostat's cooler as this is always the coldest area of the cryostat chamber when it is in operation.

Finally, it was also recognized that the effect of disinfection of the frost deposited layer is considerably more effective than a condensate of disinfection agent that is precipitated at above 0° C. as droplets. It was thus discovered that the disinfection agent requirement could be reduced by approximately a factor of 10. This reduction in the quantity of disinfection agent applied also meant that the disinfection agent precipitated in the colder area, such as the cooler, did not have to be removed and drained away again after each disinfection, as the disinfection agent layer forming there, due to the considerably smaller disinfection agent quantity applied after one disinfection operation, only corresponds to approximately one tenth of that required in the procedure described above according to the prior art. This makes it possible to perform thawing sporadically in the colder area, that is, the cooler, because a layer that has to be removed before it impairs the ability of the cold generator to operate only forms there after several disinfection operations.

Consequently, the invention eliminates both the need to heat the cryostat chamber to perform disinfection before the disinfection agent is introduced and the time-consuming removal of the disinfection agent from the cryostat chamber after each disinfection. In the prior art described above, the latter involved cooling the cooler to below 0° C. so that the disinfection agent precipitates there, followed by thawing of the cooler so that the disinfection agent can drain away, and finally generating coldness again so that the cryostat chamber returns to its operating temperature.

According to this invention, by contrast, the cryostat chamber can remain at its usual operating temperature when the disinfection agent is introduced. Depending on the type of specimens to be processed, this temperature may be anywhere between −10° C. and −35° C., usually approx. −20° C. Because, at normal operating temperatures, the cooler is usually colder anyway, the frost disinfection precipitation is sublimed into the cooler, it being sufficient if the latter is a few ° C. cooler than the microtome and cryostat chamber. The microtome can then be restarted once the layer on the microtome blade has substantially been removed. Sublimation of the disinfection agent precipitated in the other parts of the cryostat chamber can be left incomplete, as the process will be completed when the microtome cryostat is in operation again and the disinfection agent that has precipitated on the cold generator can be drained away later by sporadic defrosting phases of the cold generator.

It is perfectly sufficient if the action of sporadic thawing and draining away of the disinfection agent that has precipitated in the colder area (cooler) is performed after approx. six to ten disinfection operations, so that this operation can be advantageously scheduled at the end of the working day in order to avoid loss of operating time of the microtome cryostat.

Advantageous embodiments of the inventive method are stated in the dependent claims.

In order to perform disinfection of the microtome cryostat quickly, conditions are provided for the disinfection agent to be introduced into the cryostat chamber at the usual operating temperature; this eliminates the need for the thawing and heating-up time of the prior art described above. The usual cooling of the cryostat chamber is not interrupted when disinfection is performed but is used for the sublimation effect, because the difference in temperature between the cryostat chamber cooled to the operating temperature and the cold generator cooling the cryostat chamber is so large that the sublimation effect described above is achieved.

Introduction of the nebulized disinfection agent advantageously takes approx. three minutes, as it has been shown that this is sufficient to kill all germs present. It is sufficient because the required thickness and completeness of cover of the frost deposit is achieved and this deposit remains on the surfaces to be disinfected for the necessary length of time. In addition to the time required to introduce the disinfection agent, a certain time is required until the microtome blade has become substantially cleared as the result of sublimation. However, the sublimation time is only partly required for the disinfection action, so that, in further embodiments of the invention, this time can be reduced.

It has been shown that it is sufficient if 15 to 25 ml of disinfection agent is introduced into the cryostat chamber in the inventive method. As stated above, this is considerably less than for the prior art described above, in which approx. 200 ml of disinfection agent was required. It is precisely this reduced quantity that makes it possible to exploit the sublimation effect, to dispense with greater heating to achieve evaporation, and nevertheless to save time.

The frost deposit of the disinfection agent is all the more effective the smaller the particle size of disinfection agent introduced as a mist. In order to achieve this smallest possible particle size, it is advantageous if the disinfection agent is nebulized by ultrasound before being introduced into the cryostat chamber.

As already mentioned, the cold generator of microtome cryostat is advantageously used as the colder area. In order to thaw and drain away the disinfection agent deposited there, it is heated at sporadic intervals frequent enough to avoid the formation of a layer of frozen disinfection agent that would impair the ability of the cold generator to function, removing the disinfection agent before it reaches a critical depth. Generally, the extent of the thawing achieved after six to ten disinfection operations is quite adequate. Thus, thawing and drainage of the disinfection agent can be performed once per day.

The number of times disinfection agent is introduced into the equipment depends both on the number of specimens to be processed and on the level of the risk of infection from the specimens. It is therefore advantageous if introduction of disinfection agent is started whenever disinfection is required, wherein this is advantageously activated by the operating personnel who can estimate this requirement. However, to ensure a minimum degree of disinfection, it is advantageous if the disinfection agent is automatically introduced at least once per day.

After each disinfection operation, the microtome can then be restarted when the frost disinfection agent layer on the microtome blade has been substantially removed. Complete removal is not always necessary. Any residual layer of disinfection agent on the other surfaces of the cryostat chamber is quite harmless as it can sublime to the cold generator during subsequent sectioning operations.

In an advantageous embodiment, in order to restart the microtome more quickly after disinfection, the frost disinfection agent deposit can be removed from the microtome blade mechanically after the necessary disinfecting time. This can be performed both manually with a brush or using a suitable mechanical device. Another possibility is to accelerate removal of the disinfection agent layer from the microtome blade after the necessary disinfecting time by heating it. The temperature would not have to be raised above 0° C.; even raising the temperature just a few degrees Celsius accelerates the sublimation effect considerably. Since the microtome blade is the part of the microtome cryostat that must have a low enough temperature in order to function, it is advantageous if, after such heating, return to the low operating temperature of the microtome blade is accelerated by cooling. In this way, interruption of work by disinfection is again considerably reduced.

For disinfection at low operating temperatures, use of a hydrogen peroxide solution in water has proven to be an effective disinfection agent. The effect of disinfection at such low temperatures is then particularly effective if this hydrogen peroxide solution contains a small proportion of silver.

In accordance with the aforementioned embodiment of the inventive method, in a further embodiment of the inventive device, the nebulization device is equipped with an ultrasound generator in order to produce a mist-like fineness with ultrasound that is particularly effective. In order to access all parts of the cryostat chamber with the disinfection agent and thus particularly effectively the microtome, it is advantageous if the apparatus for the provision and introduction of a disinfection agent comprises a ventilator that applies the nebulized disinfection agent in the cryostat chamber from above.

Because sporadic thawing of the cold generator should not last too long either, it is advantageous if the latter comprises a heating facility to ensure fast thawing. It is therefore also advantageous if the cold generator comprises a collection facility to collect the thawed disinfection agent in order to drain it out of the cryostat chamber by means of the draining facility.

An input unit is preferably provided to start introduction of the disinfection agent manually, so that the operating personnel can actuate it as required, more frequently in particular when the risk of infection is especially high. In any case, the control should be constituted such that the disinfection agent is introduced at least once per day. This can be considered as the usual minimum disinfection, which should even be performed if specimens are processed that pose little risk of infection.

Furthermore, the control should be constituted such that it triggers thawing of the cold generator once per day. Of course, this does not exclude the possibility of thawing being performed more frequently, but under normal operating conditions it ensures that the layer of frozen disinfection agent on the cold generator does not become too deep. Furthermore, the end of the working day can be used in this way to ensure that thawing operations do not interrupt work during the day. Obviously, a sensor can be provided that senses and displays the thickness of the layer of frozen disinfection agent on the cold generator and/or triggers thawing.

Interruptions in work by disinfection operations can be reduced by equipment for accelerating the removal of frost deposit of a disinfection agent on the microtome blade after the necessary disinfecting time, which may last a few minutes. This can be a device for the mechanical removal of the frost deposits, or the device can take the form of a heater for the microtome blade. Such a heater can also be linked to a cooling device for the microtome blade in order to cool the microtome blade down to its operating temperature as quickly as possible after the frost deposits have been removed. A Peltier device is suitable for achieving heating and cooling with a single element.

The device is advantageously optimized for the handling of a hydrogen peroxide solution used as the disinfection agent, especially those with a small proportion of silver. This optimization comprises both the disinfecting time for reliable disinfection and the time necessary for the sublimation of such a hydrogen peroxide solution. Accordingly, the times and temperatures must be adapted to such a hydrogen peroxide solution.

Of course, embodiments disclosed for the method only can also be implemented in a suitable way for the device, and vice versa. Further embodiments are possible, for example, comprising multiple cold generators in order to further reduce, for example, the temperature of the specimen and the blade for sectioning particular specimens, in which case it must be ensured that sublimation only takes place to an even colder area (cold generator).

BRIEF DESCRIPTION OF THE DRAWING

The sole FIGURE depicts an example of an embodiment of the inventive device.

DESCRIPTION OF THE PREFERRED EMBODIMENT

The drawing shows a microtome cryostat 1 and a cryostat chamber 2 that comprises the microtome 4 that sections frozen specimens 19 using a microtome blade 5. The cryostat chamber 2 contains a cold generator 7, which serves as the colder area 6 for the purposes of the inventive method. The cold generator 7 is operated with a supply of coolant 16 that is located outside the cryostat chamber 2.

A device 8 for the provision and introduction of a disinfection agent 3 is used to disinfect the microtome cryostat 1, as is indicated by the arrows 3'. A ventilator 14 ensures the even application of the disinfection agent 3 in the cryostat chamber 2. In order to achieve a frost layer of the disinfection agent 3 in the cryostat chamber 2 that is as homogeneous and fine as possible, the device 8 is equipped with a nebulization device 8', which preferably operates with ultrasound.

A collection facility 13 is located underneath the cold generator 7, into which the thawed disinfection agent 3 runs when the cold generator 7 is defrosted. The disinfection agent 3 is transferred from this collection facility 13 to a draining facility 10 that drains the disinfection agent 3 out of the cryostat chamber 2 and into, for example, a collection vessel 18 for the thawed fluid.

A control 9 and an input unit 12 are provided for the operation of the device and execution of the method. The control 9 comprises connecting cables 17 that lead to device 8 for the provision and introduction of a disinfection agent 3, where they connect, for example, the nebulization device 8' and the ventilator 14. Furthermore, a connecting cable 17 also leads to the coolant supply 16 of the cold generator 7, and additionally to a heating facility 11 for the cold generator 7. A further connecting cable 17 leads to a Peltier device 15 that is disposed on the microtome blade 5.

The device functions as follows:

If, after sectioning the specimens 19, disinfection is required to kill germs, the device 8 is started up with the nebulization device 8' and the ventilator 14 in order to introduce the disinfection agent 3 into the cold cryostat chamber 2 in the direction of the arrows 3'. The cryostat chamber 2 is at the usual operating temperature, which can be between −10 and −35° C., usually, however, it is at approx. −20° C. The nebulized, finely distributed disinfection agent 3 then precipitates throughout the cryostat chamber 2. It suffices if introduction of the nebulized disinfection agent 3 takes approx. three minutes and during this time 15 to 25 ml of disinfection agent 3 is introduced into the cryostat chamber 2. Because the cold generator 7 continues to operate, it forms a colder area 6, which triggers sublimation of the disinfection agent 3 that has precipitated in the cryostat chamber 2. Consequently, the frost deposit of disinfection agent 3 in the cryostat chamber 2 sublimes and is deposited on the cold generator 7 that only has to be a few degrees colder for this to occur. When, after this process, the microtome blade 5 is free or substantially free of the frost deposit of the disinfection agent 3, the next specimen 19 can be sectioned.

The time it takes to remove the frost deposit from the microtome blade 5 can be reduced by using a suitable device or simply a brush to remove the frost deposit. This makes it possible to perform the next sections after only a few minutes of disinfecting time of the disinfection agent. However, the microtome blade 5 can also be equipped with a heating facility to accelerate sublimation at this location. In the depicted example embodiment, this is a Peltier device 15, with which, to accelerate sublimation, or to effect thawing and vaporization locally on the microtome blade 5 only, the microtome blade 5 can be heated up and then cooled down again briefly to restore it to its operating temperature very quickly for the next cut.

As the inventive method requires relatively little disinfection agent 3 for disinfection, it is not necessary to thaw the cold generator 7 after each disinfection operation. It is not even necessary for the entire frost deposit of the cryostat chamber 2 to be sublimed to the cold generator 7 before continuing with sectioning; it is perfectly sufficient if the microtome blade 5 is substantially free of the frost deposit, as sublimation from the remaining surfaces of the cryostat chamber 2 to the cold generator 7 continues and is completed while sectioning is in progress. The cold generator 7 should only be thawed after several disinfection operations, for example, after six to ten, to ensure that the layer of frozen disinfection agent 3 that has formed there does not prevent coldness generation. Between approximately six and ten disinfection operations are performed for average specimens 19 on one day, so that thawing of the cold generator 7 can usually be performed at the end of a working day. For this, a heating facility 11 that raises the temperature of the switched-off cold generator 7 above 0° C. is used, which thus thaws the disinfection agent 3 that has collected on the cold generator 7. The disinfection agent 3 then runs into the collection facility 13 and is drained into a collection vessel 18 for the thawed liquid located outside the cryostat chamber 2 by means of the draining facility 10. The microtome cryostat 1 can subsequently be cooled down again and restarted.

The drawing merely shows one possible embodiment of a microtome cryostat 1 functioning according to the invention. In particular, variations in the configuration are possible, the drawing being only a symbolic representation.

LIST OF REFERENCES

1 Microtome cryostat
2 Cryostat chamber
3 Disinfection agent
4 Microtome
5 Microtome blade
6 Colder area
7 Cold generator
8 Device for the provision and introduction of a disinfection agent
8' Nebulization device
9 Control
10 Draining facility
11 Heating facility
12 Input unit
13 Collection facility
14 Ventilator
15 Peltier device
16 Coolant supply for cold generator
17 Connecting cables of control
18 Collection vessel for thawed liquid
19 Specimen

I claim:

1. A method for disinfecting a microtome cryostat having a cryostat chamber, the method comprising the steps of:
   a) selecting a disinfection agent that is effective below 0° C.;
   b) introducing the disinfection agent selected in step a) as a mist into the cryostat chamber, the cryostat chamber thereby having a temperature which is below 0° C. and which is also sufficiently low as to induce collection of the disinfection agent on surfaces of the cryostat chamber as a disinfection agent frost deposit;
   c) waiting a period of time sufficient to permit action of the disinfection agent frost deposit in the cryostat chamber;
   d) displacing the frost deposit into a colder area of the cryostat chamber by sublimation;
   e) converting the disinfection agent to liquid by sporadic defrosting phases of the colder area; and
   f) removing the disinfection agent by drainage, away from the colder area.

2. The method of claim 1, wherein the disinfection agent is introduced to the cryostat chamber at a normal operating temperature thereof.

3. The method of claim 1, wherein the disinfection agent is nebulized and introduction of the nebulized disinfection agent into the cryostat chamber takes approximately three minutes.

4. The method of claim 1, wherein 15 to 25 ml of disinfection agent are introduced into the cryostat chamber.

5. The method of claim 1, wherein a nebulization of the disinfection agent is achieved by means of ultrasound before being introduced into the cryostat chamber.

6. The method of claim 1, wherein a cooling element is used as the colder area, which is heated at sporadic intervals for thawing and draining away of the disinfection agent precipitated there such that a frozen disinfection agent layer cannot develop to such a depth as to impair function of the cooling element.

7. The method of claim 6, wherein thawing and draining away is performed once per day.

8. The method of claim 1, wherein introduction of disinfection agent is performed when disinfection is required.

9. The method of claim 8, wherein introduction of the disinfection agent is performed automatically at least once per day.

10. The method of claim 1, wherein the microtome is restarted when the frost deposit of disinfection agent on a microtome blade has been substantially removed.

11. The method of claim 10, wherein removal of the frost deposit of the disinfection agent on the microtome blade after a necessary disinfecting time is performed mechanically in order to restart the microtome more quickly after disinfection.

12. The method of claim 10, wherein removal of the disinfection agent layer from the microtome blade after a necessary disinfecting time is accelerated by heating up the blade.

13. The method of claim 12, wherein return to an operating temperature of the microtome blade is accelerated by cooling the blade.

14. The method of claim 1, wherein a hydrogen peroxide solution is used as the disinfection agent.

15. The method of claim 14, wherein the solution contains a small proportion of silver.

16. A device for disinfecting a microtome cryostat, the microtome cryostat having a cryostat chamber holding a microtome, the device comprising:
   a nebulization element, said nebulization element structured to introduce a disinfection agent into the cryostat chamber as a mist;
   a cooling element, said cooling element structured to cool the cryostat chamber to a disinfecting temperature, said disinfecting temperature being below 0° C. and also being sufficiently low as to induce collection of the disinfection agent on surfaces of the cryostat chamber as a disinfection agent frost deposit, said cooling element also configured to collect the frost deposit of disinfection agent by sublimation, wherein the disinfection agent thereby forms a layer deposited on the cooling element;
   a control, said control communicating with said nebulization element and with said cooling element, said control having a timing mechanism, said control being configured to trigger introduction of the disinfection agent by said nebulization element when the cryostat chamber is at said disinfecting temperature, said timing mechanism being configured to wait a period of time sufficient to permit action of the disinfection agent frost deposit in the cryostat chamber, said control also being configured to trigger sporadic defrosting phases of said cooling element for converting the disinfection agent layer collected on the cooling element to liquid before that layer reaches a thickness that would impair function of said cooling element; and a drain for removing the disinfection agent by drainage away from said cooling element.

17. The device of claim 16, wherein said nebulization element produces fineness of the mist by means of ultrasound.

18. The device of claim 16, wherein said nebulization element comprises a ventilator that applies nebulized disinfection agent into the cryostat chamber from above.

19. The device of claim 16, wherein said cooling element comprises a heating element to accelerate thawing.

20. The device of claim 16, wherein said cooling element has a collection element for guiding thawed disinfection agent to said drain.

21. The device of claim 16, further comprising an input unit for manually starting introduction of the disinfection agent.

22. The device of claim 16, wherein the control is constituted in such a way that introduction of the disinfection agent is triggered at least once per day.

23. The device of claim 16, wherein the control is constituted to trigger thawing of said cooling element once per day.

24. The device of claim 16, further comprising a removal element, said removal element configured for removal of the frost deposit of disinfection agent on a microtome blade after a necessary disinfecting time.

25. The device of claim 24, wherein said removal element is configured for mechanical removal of the frost deposit.

26. The device off claim 24, wherein said removal element comprises a heating device for the microtome blade.

27. The device of claim 26, wherein said removal element further comprises a cooling device that cools the microtome blade after removal of the frost deposit.

28. The device of claim 24, wherein said removal element comprises a Peltier device.

29. The device of claim 16, wherein the disinfection agent is a hydrogen peroxide solution.

* * * * *